United States Patent [19]
Jones et al.

[11] Patent Number: 5,174,965
[45] Date of Patent: Dec. 29, 1992

[54] SPECIMEN CUP AND HOLDER

[76] Inventors: Timothy B. Jones, 10300 S. Western Apt. 1314, Oklahoma City, Okla. 73139; Robert D. Jones; Lori D. Jones, both of 1452 N. Washington, Ardmore, Okla. 73401

[21] Appl. No.: 679,267

[22] Filed: Apr. 2, 1991

[51] Int. Cl.⁵ .............................................. B01L 3/00
[52] U.S. Cl. .................................... 422/102; 422/104; 215/100 A; 220/737; 220/738; 220/318; 220/756; 229/1.5 B; 229/1.5 H; 294/30
[58] Field of Search ................ 422/102, 104; 206/217; 220/94 A, 96 R, 737, 738; 229/1.5 B, 1.5 H; 128/760, 761, 767; 215/100 A; 294/30

[56] References Cited
U.S. PATENT DOCUMENTS 2,641,403 6/1953 Buttery et al. .................... 229/1.5 B
3,967,848 7/1976 Sowle ........................ 229/1.5 H X Primary Examiner—James C. Housel
Assistant Examiner—Maureen M. Wallenhorst
Attorney, Agent, or Firm—Glen M. Burdick; Bill D. McCarthy

[57] ABSTRACT

A specimen gathering device is disclosed which permits a person to position the specimen gathering device for receipt of a specimen without contact with the specimen. Broadly, the specimen gathering device includes a container member and a handle assembly. The handle assembly is provided with a gripping portion which is selectively movable between a first position and a second position. In the first position the gripping portion is disposed substantially adjacent the container member; whereas, in the second position the gripping portion extends outwardly and upwardly form the container member. Thus, when the handle assembly is in the second position, a person grasping the gripping portion of the handle assembly can readily position the container member for receipt of the specimen without contact with the specimen. A specimen cup holder is also provided which comprises a cup engaging member having a handle assembly connected thereto such that the handle assembly can be selectively moved between a first position and a second position.

18 Claims, 3 Drawing Sheets

U.S. Patent    Dec. 29, 1992    Sheet 1 of 3    5,174,965
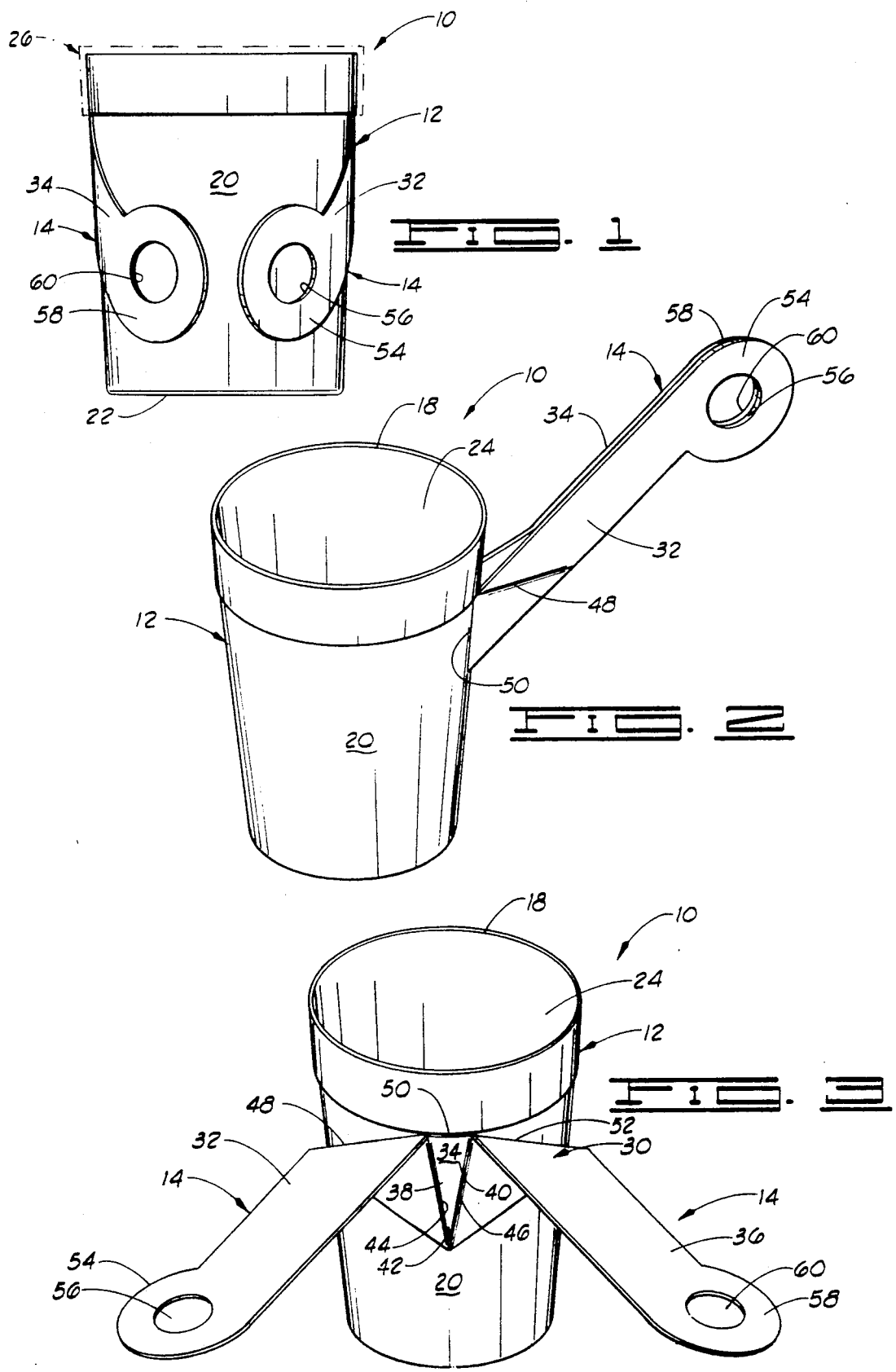

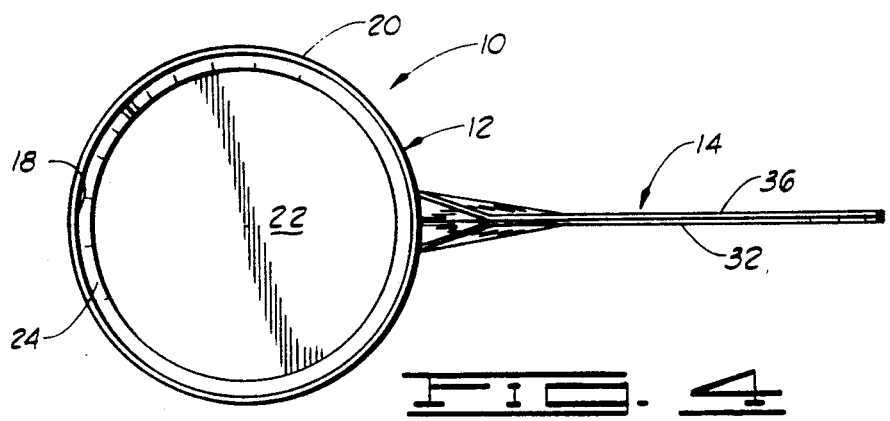
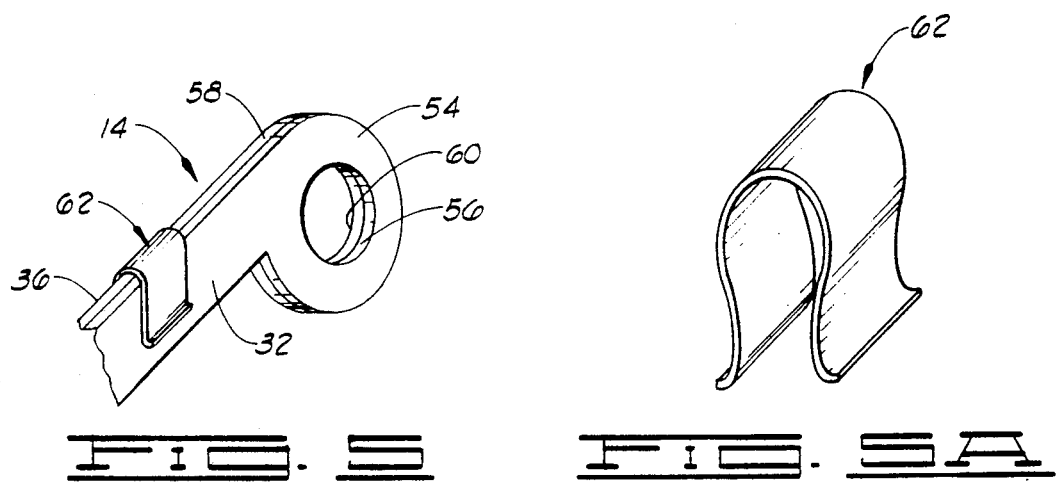
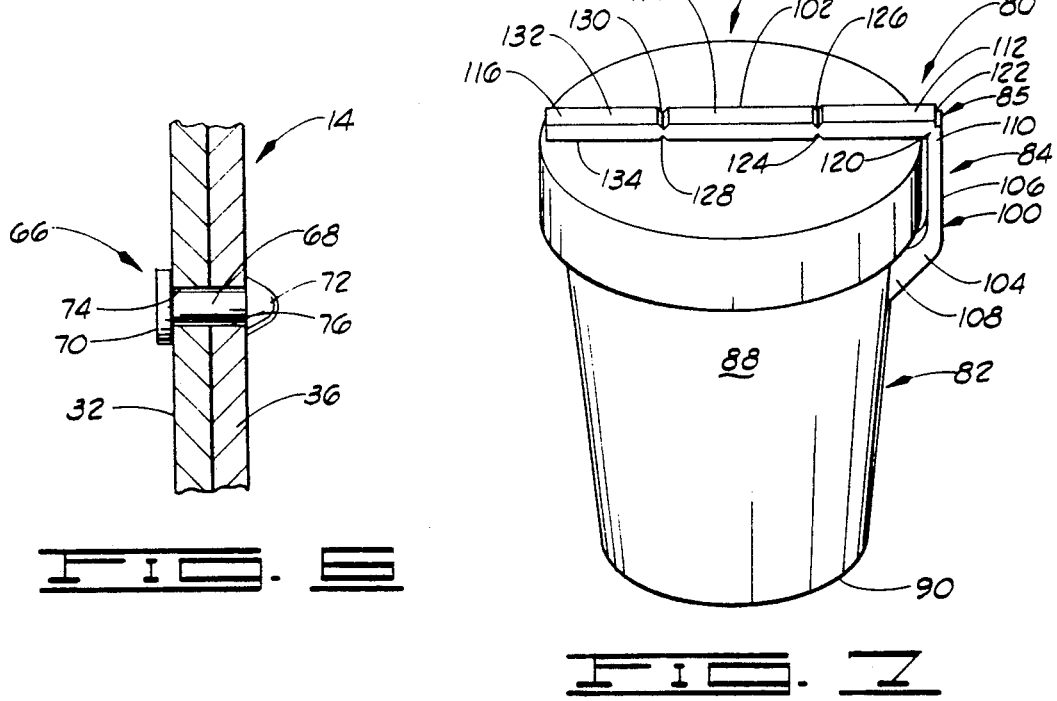

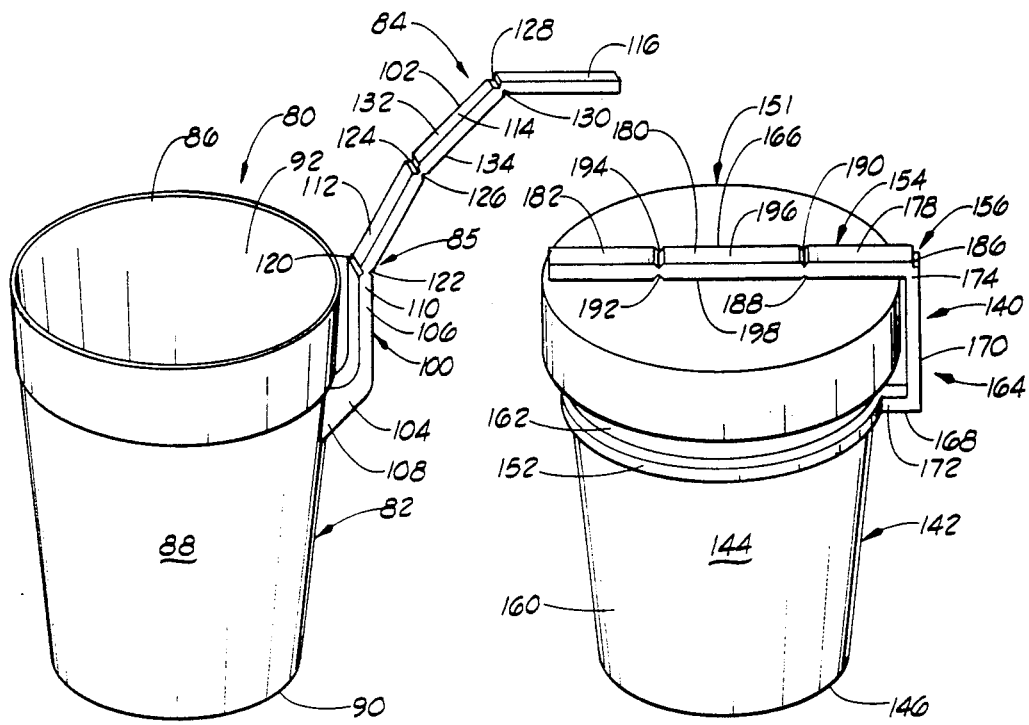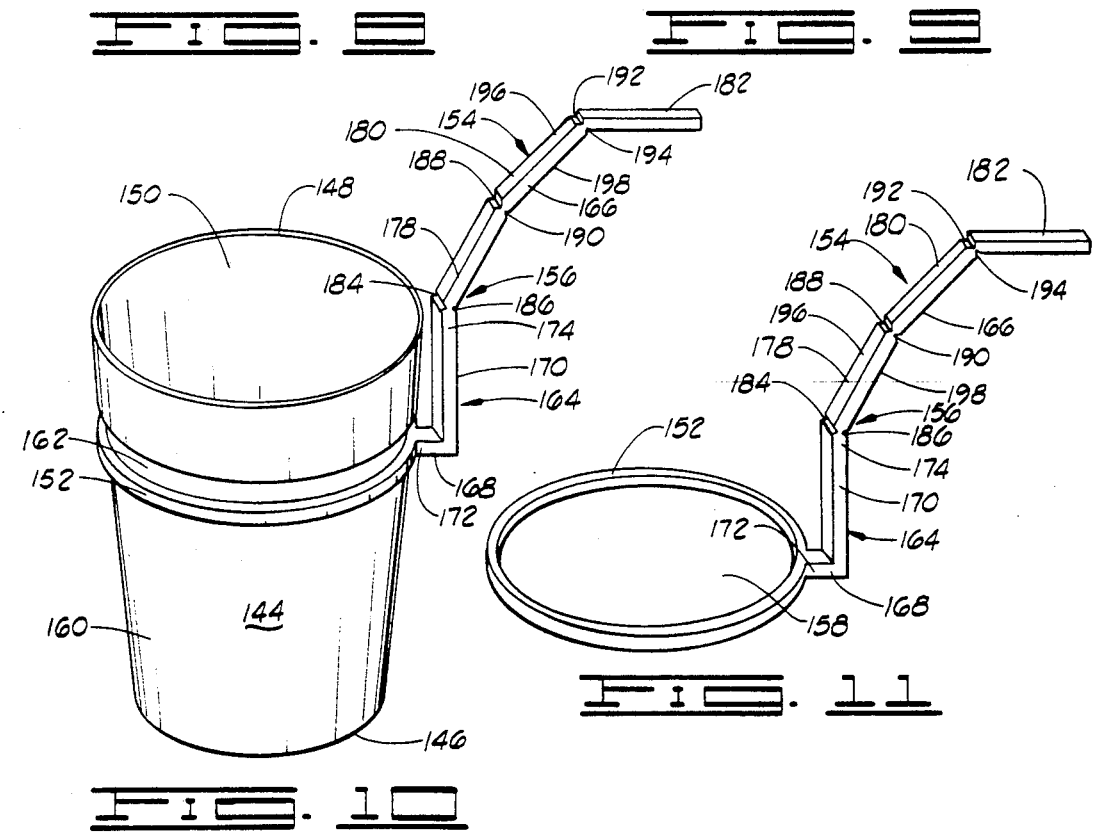

1

SPECIMEN CUP AND HOLDER

BACKGROUND OF THE INVENTION

1. Field of the Invention

The present invention relates generally to a specimen gathering device, and more particularly but not by way of limitation, to a specimen cup having a handle assembly adapted to extend upwardly and outwardly from the specimen cup. In another aspect the present invention relates to an improved holder for a specimen cup.

2. Brief Description of the Prior Art

Specimen cups and other specimen gathering devices have heretofore found wide use in the medical profession for obtaining specimens, such as urine, which must be analyzed to diagnose illnesses prior to implementing a desired medical treatment. The specimen cups heretofore available have required that a person grasp the specimen cup when obtaining the specimen. This not only gives rise to an unpleasant and often difficult situation, but many times results in contact with the specimen during the gathering of same.

Thus, it is highly desirable that improvements be made in specimen cups and other specimen gathering devices which substantially eliminate contact with the specimen while obtaining the specimen. Another desirable improvement would be to provide improved stability to the specimen cup while permitting one to more easily position the specimen cup for receipt of a specimen. However, such improved specimen cup or specimen gathering device must be simple in construction so as to enable persons of all ages to utilize the specimen cup and/or specimen gathering device, while at the same time being economical to manufacture. It is to such an improved specimen cup and specimen cup holder that the subject invention is directed.

SUMMARY OF THE INVENTION

The present invention relates to an improved specimen gathering device which permits a person to position the specimen gathering device for receipt of a specimen without contact with the specimen. Broadly, the present invention relates to an improved specimen cup comprising a container or cup member and a handle assembly which permits one to more easily position the container member for receipt of the specimen.

The handle assembly of the specimen cup of the present invention is provided with a gripping portion which is selectively movable between a first position and a second position. In the first position the gripping portion is disposed substantially adjacent the container member; whereas, in the second position the gripping portion extends outwardly and upwardly from the container member. Thus, when the handle assembly is in the second position, a person grasping the gripping portion of the handle assembly can readily position the container member for receipt of the specimen without contact with the specimen.

In another aspect the present invention relates to an improved specimen cup holder adapted to supportingly receive a specimen cup. Broadly, the specimen cup holder comprises a cup engaging member having a hollow assembly connected thereto such that the handle assembly can be selectively moved between a first position and a second position. In the first position the handle assembly is disposable across the cup engaging member as well as an open upper end of the specimen cup supported by the cup engaging member; whereas, in the second position the handle assembly extends upwardly and outwardly from the cup engaging member and thus the specimen cup is supported by the cup engaging member so that a person grasping the handle assembly can easily position the specimen cup for receipt of a specimen without contact with the specimen.

An object of the present invention is to provide an improved specimen cup which permits a person to gather a specimen without contact with the specimen.

Another object of the present invention, while achieving the before stated object, is to provide an improved specimen cup holder adapted to supportingly receive a specimen cup which will permit a person to quickly and easily position the specimen cup for receipt of a specimen without contact with the specimen.

Yet another object of the present invention, while achieving the before stated objects, is to provide an improved specimen cup and specimen cup holder which are economical to manufacture, overcome many of the problems heretofore present in the use of the prior art specimen gathering devices, and which are durable in construction.

Other objects, features and advantages of the present invention will become clear upon reading the following detailed description in conjunction with the drawings and the appended claims.

BRIEF DESCRIPTION OF THE DRAWINGS

FIG. 1 is an elevational view of one side of a specimen cup of the present invention having a handle assembly thereof disposed in a first position.

FIG. 2 is a perspective view of the specimen cup of the present invention having the handle assembly thereof disposed in a second position.

FIG. 3 is a perspective view of the specimen cup of the present invention having the handle assembly thereof disposed in an intermediate position between the first and second positions.

FIG. 4 is a top plan view of the specimen cup of FIG. 2.

FIG. 5 is an enlarged, perspective view of a gripping portion of the handle assembly of the specimen cup of the present invention having a connector member connected thereto.

FIG. 5A is an enlarged, perspective view of the connector member of FIG. 5.

FIG. 6 is an enlarged cross-sectional view of the gripping portion of the handle assembly of the specimen cup of the present invention having a second embodiment of a connector member connected thereto.

FIG. 7 is a perspective view of a second embodiment of a specimen cup constructed in accordance with the present invention, the specimen cup having a closure cap, a handle assembly of the specimen cup being disposed in a first position so as to extend across and in close proximity to the closure cap.

FIG. 8 is a perspective view of the specimen cup of FIG. 7 wherein the closure cap has been removed and the handle assembly is disposed in a second position.

FIG. 9 is a perspective view of a specimen cup holder constructed in accordance with the present invention, the specimen cup holder supportingly engaging a specimen cup having a closure cap, a handle assembly of the specimen cup holder disposed in a first position so as to extend across and in close proximity to the closure cap.

FIG. 10 is a perspective view of a specimen cup holder of FIG. 9 having the closure cap removed and wherein the handle assembly is disposed in a second position.

FIG. 11 is a perspective view of the specimen cup holder of the present invention wherein the handle assembly is disposed in the second position.

DESCRIPTION

Referring now to the drawings and more particularly to FIGS. 1-4, shown therein is an improved specimen cup 10 constructed in accordance with the present invention. The specimen cup 10 comprises a container or cup member 12 and a handle assembly 14. The handle assembly 14 is hingedly connected to the container member 12 so as to be selectively movable between a first position (FIG. 1) and a second position (FIGS. 2 and 4). In the first position the handle assembly 14 is disposed substantially adjacent the container member 12; whereas, in the second position the handle assembly 14 extends outwardly and upwardly from the container member 12 so that a person grasping the handle assembly 14 can easily position the container member 12 for receipt of a specimen without contact with the specimen.

The container member 12 and the handle assembly 14 are desirably of unitary construction. However, it is to be understood that the container member 12 and the handle assembly 14 can be fabricated as separate elements, provided that the handle assembly 14 is fabricated of a material capable of being bonded or otherwise connected to the container member 12.

The container member 12, which has an open upper end 18 (FIGS. 2-4), is characterized as having a continuous side wall 20 and a bottom member 22. The continuous side wall 20 and the bottom member 22 cooperate to define a specimen receiving cavity 24 which openly communicates with the open upper end 18 of the container member 12 so that specimen can be deposited within the specimen receiving cavity 24.

The container member 12 can be provided with a closure member or cap 26 (FIG. 1) adapted to engage a portion of the continuous side wall 20 forming the open upper end 18. Thus, when the closure member 26 is connected to the container member 12, the open upper end 18 of the container member 12 is closed off and the specimen receiving cavity 24 is effectively sealed.

The container member 12 can be fabricated of any suitable substantially fluid-impervious material, such as plastic, glass and the like. Further, the container member 12 can be constructed in a variety of shapes and configurations. For example, the continuous side wall 20 of the container member 12 illustrated in FIGS. 1-4 is tapered from the open upper end 18 towards the bottom member 22. Thus, the container member 12 is provided with an inverted, substantially frusto-conical shaped configuration.

The handle assembly 14 can be fabricated of any material having sufficient strength to support the container member 12 and specimen collected therein when the handle assembly 14 is in the second position. Further, the material from which the handle assembly 14 is fabricated will desirably possess sufficient memory properties so that when the handle assembly 14 is moved from the first position to the second position, or visa versa, the handle assembly 14 will substantially remain in the desired position.

Referring more specifically to FIG. 3, the handle assembly 14 is shown as a substantially V-shaped member 30 having a first gripping portion 32, an inverted, substantially triangularly shaped medial portion 34 and a second gripping portion 36. The inverted substantially triangularly shaped medial portion 34 is characterized as having a first side 38 and a second side 40 which intersect to form an apex 42.

In order to provide the desired movement of the first and second gripping portions 32, 36 of the handle assembly 14 between the first position (FIG. 1) and the second position (FIG. 2), the first gripping portion 32 is hingedly connected to the first side 38 of the inverted, substantially triangularly shaped medial portion 34, and the second gripping portion 36 is hingedly connected to the second side 40 of the inverted, substantially triangularly shaped medial portion 34. Any suitable means can be employed for hingedly connecting the first and second gripping portions 32, 36 to the inverted, substantially triangularly shaped medial portion 34 so long as such connection means permits the first and second gripping portions 32, 36 to be selectively moved between the first and second positions. For example, when the substantially V-shaped member 30 is of unitary construction and fabricated of a polymeric material, the substantially V-shaped member 30 is provided with a score line 44 along the junction of the first gripping portion 32 and the first side 38 of the inverted, substantially triangularly shaped medial portion 34, and a score line 46 along the junction of the second gripping portion 36 and the second side 40 of the inverted, substantially triangularly shaped medial portion 34.

The first gripping portion 32 is further provided with a score line 48 which extends across the width of the first gripping portion 32 so as to be aligned with a base 50 of the inverted, substantially triangularly shaped medial portion 34; and the second gripping portion 36 is also provided with a score line 52 which extends across the width of the second gripping portion 36 so as to be aligned with the base 50 of the inverted, substantially triangularly shaped medial portion 34. Thus, the score line 44 functions as a hinge for connecting the first gripping portion 32 to the first side 38 of the inverted, substantially triangularly shaped medial portion 34 so that the first gripping portion 32 can be moved outwardly from the container member 12; whereas, the score line 48 functions as a hinge so that the first gripping portion 32 can be moved upwardly relative to the container member 12. Thus, the score lines 44, 48 cooperate so that the first gripping portion 32 can be selectively moved between the first and second positions.

Similarly, the score line 46 functions as a hinge for connecting the second gripping portion 36 to the second side 40 of the inverted, substantially triangularly shaped medial portion 34 so that the second gripping portion 36 can be moved outwardly from the container member 12; whereas, the score line 52 functions as a hinge so that the second gripping portion 36 can be moved upwardly relative to the container member 12. Thus, the score lines 46, 52 cooperate so that the second gripping portion 36 can be moved between the first and second positions.

As previously stated, the substantially V-shaped member 30 is desirably of unitary construction; and the substantially V-shaped member 30 is desirably fabricated of a polymeric material possessing properties heretofore described. That is, the polymeric material must have sufficient strength to support the container member 12 when the first and second gripping portions 32, 36 are in the second position and specimen is deposited within the specimen receiving cavity 24 of the container member 12; and the polymeric material desirably possesses sufficient memory so that when the first and second gripping portions 32, 36 are moved from the first position to the second position, or visa versa, the first and second gripping portions 32, 36 will be retained in the desired position without application of external force.

To facilitate grasping of the first and second gripping portions 32, 36 of the substantially V-shaped member 30, as well as to facilitate placement of the first and second gripping portions 32, 36 in the second position, the first gripping portion 32 is provided with an enlarged distal end 54 having an opening 56 extending therethrough. Similarly, the second gripping portion 36 is provided with an enlarged distal end 58 having an opening 60 extending therethrough. Thus, when the first and second gripping portions 32, 36 are selectively moved to the second position, the enlarged distal ends 54, 58 of the first and second gripping portions 32, 36 are substantially adjacently disposed and the openings 56, 60 therein are aligned so as to facilitate grasping of the enlarged distal ends 54, 58 of the first and second gripping portions 32, 36 to stabilize the container member 12 when obtaining the specimen.

To enhance the stability of the handle assembly 14 when the first and second gripping portions 32, 36 are in the second position, it may be desirable to interconnect the first and second gripping portions 32, 36. A suitable means for interconnecting the first and second gripping portions 32, 36 (when same are in the second position) is a biased substantially U-shaped clip member 62 illustrated in FIGS. 5 and 5A. That is, when the first and second gripping portions 32, 36 are in the second position (i.e., a position wherein the first and second gripping portions extend outwardly and upwardly from the container member 12 and the first and second gripping portions 32 36 are adjacently disposed), the clip member 62 is positioned over a portion of the first and second gripping portions 32, 36 (substantially as shown in FIG. 5) so that the clip member 62 compresses against the first and second gripping portions 32, 36 and frictionally engages the first and second gripping portions 32, 36. Thus, the clip member 62 provides a convenient means for interconnecting the first and second gripping portions 32, 36 of the handle assembly 14 (when same are in the second position) and thereby assists in stabilizing and strengthening the handle assembly 14 and thus the container member 12.

Referring now to FIG. 6, a connector assembly 66 for connecting the first and second gripping portions 32, 36 of the handle assembly 14 when the first and second gripping portions 32, 36 are in the second position is illustrated. The connector assembly 66 comprises a pin member 68 having an enlarged head portion 70 and an enlarged distal end portion 72. The enlarged distal end portion 72 is provided with a cone-like configuration substantially as shown.

In order to connect the first and second gripping portions 32, 36, of the handle assembly 14 utilizing the connector assembly 66, each of the first and second gripping portions 32, 36 is provided with an aperture 74 and 76, respectively. The apertures 74, 76 are alignable with each other when the first and second gripping portions 32, 36 are disposed in the second position. As illustrated in FIG. 6, the enlarged head portion 70 and the enlarged distal end portion 72 of the connector assembly 66 are each provided with a diameter greater than the diameter of the apertures 74, 76. Thus, because of the cone-like configuration of the enlarged distal end portion 72 the enlarged distal end portion 72 can be forced through the apertures 74, 76 so that the pin member 68 is positioned through the aligned apertures 74, 76 and the enlarged head portion 70 abuttingly engages the first gripping portion 32 and the enlarged distal end portion 72 abuttingly engages the second gripping portion 36 and securely connects the first and second gripping portions 32, 36.

Connectors, such as the connector assembly 66, are well known in the art. Thus, no further description of the connector assembly 66 is believed necessary in order to enable one skilled in the art to construct and use the connector assembly 66 in conjunction with the first and second gripping portions 32, 36 of the handle assembly 14. However, it should be understood that the connector assembly 66 and the first gripping portion 32 can be of a unitary construction and, in such event, an aperture, such as the aperture 76, is provided only in the second gripping portion 36.

Referring now to FIGS. 7 and 8, a second embodiment of an improved specimen cup 80 constructed in accordance with the present invention is illustrated. The specimen cup 80 comprises a container or cup member 82 and a handle assembly 84 for supporting and facilitating placement of the container member 82 in a desired position to receive a specimen. The handle assembly 84 is provided with at least one hinge assembly 85 so that the handle assembly 84 can be disposed in either a first position (FIG. 7) or a second position (FIG. 8).

The container member 82, which has an open upper end 86 (FIG. 8), is provided with a continuous side wall 88 and a bottom member 90. The continuous side wall 88 is tapered from the open upper end 86 of the container member 82 towards the bottom member 90 and cooperates with the bottom member 90 to define a specimen receiving cavity 92 which openly communicates with the open upper end 86.

The container member 82 is further provided with a closure member or cap 94 (FIG. 7) adapted to engage a portion of the continuous side wall 88 forming the open upper end 86. Thus, when the closure member 94 is connected to the container member 82, the open upper end 86 of the container member 82 is closed off and the specimen receiving cavity 92 is effectively sealed.

The container member 82 and the handle assembly 84 are desirably of unitary construction; and the handle assembly 84 is desirably fabricated of a polymeric material which possesses sufficient strength to support the container member 82 and specimen collected within the specimen receiving cavity 92 when the handle assembly 84 is in the second position. Further the polymeric material from which the handle assembly 84 is fabricated, desirably possesses sufficient memory so that when the handle assembly 84 is moved from the first position to the second position, or visa versa, the handle assembly 84 will remain in the desired position. While numerous polymeric materials are commercially available from which the specimen cup 80 can be fabricated, especially desirable results have been obtained where the container member 82 and the handle assembly 84 of the specimen cup 80 are fabricated of a polyolefin.

The handle assembly 84 comprises a substantially L-shaped member 100 and a handle member 102 hingedly connected to the substantially L-shaped member 100 by the hinge assembly 85 such that the handle member 102 is selectively movable between the first position (FIG. 7) and the second position (FIG. 8). In the first position the handle member 102 extends across the closure member 94 connected to the container member 82 for closing off the open upper end 86 of the container member 82 (FIG. 7); whereas, in the second position, the handle member 102 extends outwardly and upwardly from the substantially L-shaped member 100 and thus the container member 82 (FIG. 8). Thus, when the handle member 102 is in the second position a person can readily grasp the handle member 102 and position the container member 82 for receipt of a specimen without contact with the specimen.

The substantially L-shaped member 100 is characterized as having a first leg portion 104 and a substantially normally disposed second leg portion 106. One end 108 of the first leg portion 104 is connected to the continuous side wall 88 of the container member 82 such that the second leg portion 106 is substantially parallel and spatially disposed relative to an adjacently disposed portion of the continuous side wall 88 of the container member 82. The second leg portion 106 extends in an upwardly direction from the first leg portion 104 and is provided with a distal end portion 110 which terminates a selected distance above the container member 82. Thus, when the handle member 102 is hingedly connected to the distal end portion 110 of the second leg portion 106, the handle member 102 can be selectively moved between the first and second positions.

The handle member 102 is an elongated member characterized as having a first end portion 112, a medial portion portion 114 and an opposed second end portion 116. The first end portion 112 of the handle member 102 is hingedly connected to the distal end portion 110 of the second leg portion 106 of the substantially L-shaped member 100 by the hinge assembly 85. Thus, the handle member 102 can be disposed in either the first position or the second position. In the second position the opposed second end portion 116 of the handle member 102 is disposed upwardly and outwardly from the distal end portion 110 of the second leg portion 106 and thus the container member 82 substantially as shown in FIG. 8. Further, when the handle member 102 is in the second position the opposed second end portion 116 thereof constitutes a gripping portion for the handle member 102.

As previously stated, the distal end portion 110 of the second leg portion 106 of the substantially L-shaped member 100 is hingedly connected to the first end portion 112 of the handle member 102 by the hinge assembly 85 so that the handle member 102 can be selectively moved between the first and second positions.

When fabricating the handle assembly 84 of the specimen cup 80 of a polymeric material, and when the substantially L-shaped member 100 and the handle member 102 of the handle assembly 84 are fabricated of unitary construction, the hinge assembly 85 comprises a pair of oppositely disposed substantially V-shaped grooves 120, 122 formed at the junction of the distal end portion 110 of the second leg portion 106 of the substantially L-shaped member 100 and the first end portion 112 of the handle member 102 substantially as shown. The oppositely disposed substantially V-shaped grooves 120, 122, which are aligned with each other, extend transverse to the elongated axis of the handle member 102 and the second leg portion 106 of the substantially L-shaped member 100. Thus, the oppositely disposed V-shaped grooves 120, 122 function as the hinge assembly 85 for hingedly connecting the handle member 102 to the substantially L-shaped member 100 so that the handle member 102 can be selectively moved between the first position (FIG. 7) and the second position (FIG. 8).

To further enhance positioning of the container member 82 for receipt of a specimen (without contact with the specimen by a person holding the specimen cup 80) the handle member 102 is desirably provided with oppositely disposed V-shaped grooves 124, 126 and oppositely disposed V-shaped grooves 128, 130. The oppositely disposed substantially V-shaped grooves 124, 126 are formed in opposite sides 132, 134 of the medial portion 114 of the handle member 102; and the oppositely disposed substantially V-shaped grooves 128, 130 are formed in the opposite sides 132, 134 of the handle member 102 a selected distance from the opposed second end portion 116 of the handle member 102 which functions as a grasping portion for the handle member 102. Each of the oppositely disposed substantially V-shaped grooves 124-130 extend transverse to the elongated axis of the handle member 102 so as to be substantially parallel with the oppositely disposed substantially V-shaped grooves 120, 122. Thus, the oppositely disposed substantially V-shaped grooves 124, 126 provide a hinge-like function for the handle member 102 which permits the opposed second end portion 116 of the handle member 102 to be further outwardly displaced from the second leg portion 106 of the substantially L-shaped member 100 and the container member 82 of the specimen cup 80; whereas the oppositely disposed substantially V-shaped grooves 128, 130 provide a hinge-like function between the medial portion 114 and the opposed second end portion 116 of the handle member 102 which permits one to position the opposed second end portion 116 of the handle member 102 in a substantially parallel position relative to the open upper end 86 of the container member 82 and thereby facilitate grasping of the opposed second end portion 116 of the handle member 102 and the positioning of the container member 82 for receipt of a specimen.

Referring now to FIGS. 9, 10 and 11, a specimen cup holder 140 constructed in accordance with the present invention is illustrated. The specimen cup holder 140 is adapted to supportingly receive a specimen gathering device, such as a specimen cup 142, so that a person can collect a specimen in the specimen cup 142 without contact with the specimen.

The specimen cup 142 is of conventional construction and comprises a continuous side wall 144 and a bottom member 146. The continuous side wall 144 is tapered from an open upper end 148 (FIG. 10) of the specimen cup 142 towards the bottom member 146 so as to define a specimen receiving cavity 150. The specimen cup 142 is illustrated in FIG. 9 as having a closure member or cap 151 adapted to engage an upper portion of the specimen cup 142 so as to effectively seal the specimen receiving cavity 150.

The specimen cup holder 140, comprises a cup engaging member, such as a ring member 152, and a handle assembly 154 connected to the ring member 152. The handle assembly 154 is provided with at least one hinge assembly 156 so that the handle assembly 154 can be selectively moved between a first position (FIG. 9) and a second position (FIGS. 10 and 11). In the first position the handle assembly 154 can be folded over the ring member 152 for storage or over the specimen cup 142 or the closure member 151 of the specimen cup 142 substantially as shown. In the second position the handle assembly 154 extends upwardly and outwardly from the ring member 152 (and thus the specimen cup 142 supported by the ring member 152) so that a person grasping the handle assembly 154 can position the specimen cup 142 for receipt of the specimen without contact with the specimen.

The ring member 152 is provided with a cup receiving opening 158 having a diameter greater than the diameter of a lower end portion 160 of the specimen cup 142 but less than the diameter of an upper end portion 162 of the specimen cup 142. Thus, when the specimen cup 142 is positioned within the cup receiving opening 158 of the ring member 152, the ring member 152 frictionally engages the continuous side wall 144 of the specimen cup 142 and secures the specimen cup 142 in a stable position.

The handle assembly 154 comprises a substantially L-shaped member 164 and a handle member 166 hingedly connected to the substantially L-shaped member 164 by the hinge assembly 156 such that the handle member 166 is selectively movable between the first and second position. The substantially L-shaped member 164 is characterized as having a first leg portion 168 and a substantially normally disposed second leg portion 170. One end 172 of the first leg portion 168 is connected to the ring member 152 so that the first leg portion 168 is substantially coplanar with the ring member 152 and the second leg portion 170 extends upwardly therefrom such that when the specimen cup 142 is positioned in the cup receiving opening 158 of the ring member 152 the second leg portion 170 is spatially disposed relative to the specimen cup 142 substantially as shown.

The second leg portion 170, which extends in an upwardly direction from the first leg portion 168, is provided with a distal end portion 174. Further, the second leg portion 170 is desirably provided with a sufficient length so that when the specimen cup 142 is positioned within the cup receiving opening 158 of the ring member 152, the distal end portion 174 of the second leg portion 170 is disposed above the specimen cup 142.

The handle member 166 is an elongated member characterized as having a first end portion 178, a medial portion 180 and an opposed second end portion 182. The first end portion 178 of the handle member 166 is hingedly connected to the distal end portion 174 of the second leg portion 170 of the substantially L-shaped member 164 by the hinge assembly 156. Thus, in order to permit the handle member 166 to be disposed in the first position (where the handle member 166 extends across and is substantially adjacently disposed to the specimen cup 142 supported by the specimen cup holder 140), the length of the second leg portion 170 of the substantially L-shaped member 164 must be sufficient to permit the movement of the handle member 166 to the first position.

As shown in FIGS. 10 and 11, when the handle member 166 is in the second position the opposed second end portion 182 of the handle member 166 is disposed upwardly and outwardly from the distal end portion 17 of the second leg portion 170 of the substantially L-shaped member 164, and thus the specimen cup 142. Further, when the handle member 166 is in the second position the opposed second end portion 182 thereof constitutes a gripping portion for the handle member 166.

The ring member 152, the handle assembly 154 and the hinge assembly 156 for hingedly connecting the handle assembly 154 to the ring member 152 are desirably of unitary construction and fabricated of a polymeric material. In such instance, the hinge assembly 156 comprises a pair of oppositely disposed substantially V-shaped grooves 184, 186 formed at the junction of the distal end portion 174 of the second leg portion 170 of the substantially L-shaped member 164 and the first end portion 178 of the handle member 166 substantially as shown. The oppositely disposed substantially V-shaped grooves 184, 186, which are aligned with each other, are transversely disposed to the elongated axis of the handle member 166 and the second leg portion 170 of the substantially L-shaped member 164. Thus, the oppositely disposed V-shaped groove 184, 186 constitute the hinge assembly 156 for hingedly connecting the handle member 166 to the substantially L-shaped member 164 so that the handle member 166 can be selectively moved between the first and second positions.

To further enhance positioning of the specimen cup 142 for receipt of a specimen (without contact with the specimen by the person holding the specimen cup 142) the handle member 166 is desirably provided with oppositely disposed V-shaped grooves 188, 190 and oppositely disposed V-shaped grooves 192, 194. The oppositely disposed V-shaped grooves 188, 190 are formed in opposite sides 196, 198 of the medial portion 180 of the handle member 166; and the oppositely disposed substantially V-shaped grooves 192, 194 are formed in the opposite sides 196, 198 of the handle member 166 a selected distance from the opposed second end portion 182 of the handle member 166 substantially as shown. Each of the substantially V-shaped grooves 188–194 extend transverse to the elongated axis of the handle member 166 so as to be substantially parallel with the substantially V-shaped grooves 184, 186. Thus, the oppositely disposed substantially V-shaped grooves 188, 190 provide a hinge-like function to the handle member 166 which permits the opposed second end portion 182 of the handle member 166 to be outwardly displaced a further distance from the second leg portion 170 of the substantially L-shaped member 164 and thus the ring member 152 and the specimen cup 142 supported therein; whereas, the oppositely disposed substantially V-shaped grooves 192, 194 provide a hinge-like function between the medial portion 180 and the opposed second end portion 182 of the handle member 166 which permits one to position the opposed second end portion 182 of the handle member 166 in a substantially parallel position relative to the ring member 152 and thus the open upper end 148 of the specimen cup 142 supported within the cup receiving opening 158 of the ring member 152. The disposition of the opposed second end portion 182 of the handle member 166 in a parallel position relative to the open upper end 148 of the specimen cup 142 facilitates grasping of the opposed second end portion 182 of the handle member 166 and thus the positioning of the specimen cup 142 for receipt of a specimen.

The specimen cup holder 140 of the present invention can be fabricated of any suitable material possessing sufficient strength to support the specimen cup 142 and specimens deposited therein. Further, the material for which the specimen cup holder 140 is fabricated desirably possesses sufficient memory so that when the handle member 166 is moved from the first position to the second position, or visa versa, the handle member 166 will remain in the desired position. While numerous materials may be commercially available from which the specimen cup holder 140 can be fabricated, especially desirable results have been obtained wherein the specimen cup holder 140 is fabricated of a polyolefin.

The specimen cups 10 and 80, as well as the specimen cup holder 140, permit one a convenient way to gather a specimen without contact with the specimen. Further, from the foregoing description, it is clear that the present invention is well adapted to carry out the objects and obtain the ends and advantages as well as those inherent therein. While presently preferred embodiments of the invention have been described for purposes of this disclosure, numerous changes may be made which will readily suggest themselves to those skilled in the art, which changes are encompassed within the spirit of the invention disclosed and as defined in the appended claims herein.

What is claimed is:

1. A specimen cup comprising:
   container means for receiving and retaining a specimen,
   the container means defining a specimen receiving cavity and having an open upper end communicating with the specimen receiving cavity;
   handle means for supporting and positioning the container means to receive specimen within the specimen receiving cavity, the handle means comprising a substantially V-shaped member having a first gripping portion, an inverted, substantially triangularly shaped medial portion and a second gripping portion, the substantially triangularly shaped medial portion having a first side and a second side which intersect to form an apex of the inverted, substantially triangularly shaped medial portion, the first and second gripping portions being selectively movable between a first position and a second position, in the first position the gripping portions of the handle means disposed substantially adjacent the container means, in the second position the gripping and portions of the handle means extending outwardly and upwardly from the container means so that a person grasping the gripping portions can readily position the container means for receipt of the specimen without contact with the specimen;
   first hinged means for connecting the first gripping portion of the substantially V-shaped member to the first side of the inverted, substantially triangularly shaped medial portion such that the first gripping portion is selectively movable between the first and second positions; and
   second hinged means for connecting the second gripping portion of the substantially V-shaped member to the second side of the inverted, substantially triangularly shaped medial portion such that the second gripping portion is selectively movable between the first and second positions.

2. The specimen cup of claim 1 wherein each of the first and second gripping portions is provided with an enlarged distal end having an opening extending therethrough such that when the first and second gripping portions are selectively moved to the second position, the enlarged distal ends of the first and second gripping portions are substantially adjacently disposed and the openings therein are aligned so as to enhance grasping of the enlarged distal ends of the first and second gripping portions and thereby stabilize the container means when obtaining the specimen.

3. The specimen cup of claim 2 wherein the inverted, substantially triangularly shaped medial portion is further characterized as having a base extending between the first and second sides thereof, the base spatially disposed from the open upper end of the container means so as to be substantially parallel with the open upper end of the container means, and wherein the first hinge means comprises:
   a first score line extending across the width of the first gripping portion, the first score line being aligned with the base of the inverted, substantially triangularly shaped medial portion;
   an angularly disposed second score line extending along the first side of the inverted, substantially triangularly shaped medial portion; and
   wherein the second hinge means comprises:
   a first score line extending across the width of the second gripping portion, the first score line being aligned with the base of the inverted, substantially triangularly shaped medial portion; and
   an angularly disposed second score line extending along the second side of the inverted, substantially triangularly shaped medial portion.

4. The specimen cup of claim 3 wherein the substantially V-shaped member is of unitary construction fabricated of a polymeric material having sufficient strength to support the container means when the first and second gripping portions of the substantially V-shaped member are in the second position and specimen is deposited in the specimen receiving cavity of the container means.

5. The specimen cup of claim 4 further comprising:
   connector means for connecting the first and second gripping portions of the substantially V-shaped member when the first and second gripping portions are in the second position.

6. The specimen cup of claim 1 wherein the inverted, substantially triangularly shaped medial portion of the substantially V-shaped member is further characterized as having a base extending between the first and second sides thereof, the base spatially disposed from the open upper end of the container means so as to be substantially parallel with the open upper end of the container means, and wherein the first hinge means comprises:
   a first score line extending across the width of the first gripping portion, the first score line being aligned with the base of the inverted substantially triangularly shaped medial portion; and
   an angularly disposed second score line extending along the first side of the inverted, substantially triangularly shaped medial portion; and
   wherein the second hinge means comprises:
   a first score line extending across the width of the second gripping portion, the first score line being aligned with the base of the inverted, substantially triangularly shaped medial portion; and
   an angularly disposed second score line extending along the second side of the inverted, substantially triangularly shaped medial portion.

7. The specimen cup of claim 6 wherein the substantially V-shaped member is of unitary construction fabricated of a polymeric material having sufficient strength to support the container means when the first and second gripping portions of the substantially V-shaped member are in the second position and specimen is deposited in the specimen receiving cavity of the container means.

8. The specimen cup of claim 1 further comprising: closure means connectable to the container means for closing the open upper end of the container means.

9. A specimen cup comprising:

container means for receiving and retaining a specimen, the container means comprising a substantially cylindrically shaped cup member having a container side wall defining a specimen receiving cavity, and an open upper end openly communicating with the specimen receiving cavity;

handle means for supporting and positioning the cup member to receive specimen within the specimen receiving cavity, the handle means having a gripping portion selectively movable between a first position and a second position, in the first position the gripping portion extending across at least a portion of the open upper end of the cup member so as to be substantially adjacently disposed thereto, in the second position the gripping portion extending outwardly and upwardly from the container means, the handle means comprising:

a substantially L-shaped member having a first leg portion and a second leg portion, the first leg portion connected to the cup member a selected distance from the open upper end of the cup member such that the first leg portion is substantially normally disposed relative to an adjacently disposed portion of the continuous sidewall of the cup member, the second leg portion being substantially parallel to the continuous sidewall of the cup member and extending in an upwardly direction;

a handle member having a first end portion, a medial portion and an opposed second end portion, the opposed second end portion constituting the gripping portion of the handle means; and first hinge means for hingedly connecting the first end portion of the handle member to the second leg portion of the substantially L-shaped member such that the handle means is selectively movable between the first and second positions.

10. The specimen cup of claim 9 further comprising:

at least one second hinge means supported by the handle member for permitting the handle member to be further moved in an outward direction from the cup member to enhance positioning of the cup member when obtaining the specimen.

11. The specimen cup of claim 10 wherein the L-shaped member and the handle member are of unitary construction and the handle member is further characterized has having a first side and an opposed second side, and wherein the first hinge means comprises:

a first V-shaped notch formed at a junction of the second leg portion of the substantially L-shaped member and the first end portion of the handle member via the first side thereof, the first V-shaped notch transversely disposed to an elongated axis of the handle member: and a second V-shaped notch formed at a junction of the second leg portion of the substantially L-shaped member and the first end portion of the handle member via the second side of the handle member, the second V-shaped notch transversely disposed to the elongated axis of the handle member and aligned with the first V-shaped notch.

12. The specimen cup of claim 11 wherein the second hinge means comprises at least one substantially V-shaped notch formed in the medial portion of the handle member via at least one side thereof, the V-shaped notch being normally disposed relative to the elongated axis of the handle member.

13. The specimen cup of claim 12 wherein the substantially L-shaped member and the handle member are of unitary construction fabricated of a polymeric material having sufficient strength to support the cup member when the handle member is in the second position and the specimen is deposited in the specimen receiving cavity of the cup member.

14. A specimen cup holder comprising:

specimen cup engaging means comprising ring means for supportedly receiving and frictionally engaging a portion of a continuous sidewall of a specimen cup, and handle means for supporting and positioning a continuous sidewall of a specimen cup, the handle means selectively movable between a first position and a second position, in the first position a portion of the handle means extending across at least a portion of the specimen cup engaging means so as to be substantially adjacently disposed thereto, in the second position the handle means extending outwardly and upwardly from the specimen cup engaging means, the handle means comprising:

a substantially L-shaped member having a first leg portion and a second leg portion, the first leg portion being substantially coplanar with the ring means and extending outwardly therefrom, the second leg portion being substantially normally disposed to the first leg portion so as to extend in an upwardly direction therefrom, the second leg portion terminating a predetermined distance from an open upper end of a specimen cup supported within the specimen cup engaging means, the second leg portion also disposed so as to be substantially parallel to an adjacently disposed continuous sidewall of a specimen cup supported within the specimen cup engaging means;

a handle member having a first end portion, a medial portion, and an opposed second end portion; and first hinge means for hingedly connecting the first end portion of the handle member to the second leg portion of the substantially L-shaped member such that the handle means is selectively movable between the first and second positions.

15. The specimen cup holder of claim 14 further comprising:

at least one second hinge means supported by the handle member for permitting the handle means to be further moved in an outward direction from the ring means.

16. The specimen cup holder of claim 15 wherein the substantially L-shaped member, the ring means and the handle member are of unitary construction, the handle member is further characterized as having a first side an opposed second side, and wherein the first hinge means comprises:

a first V-shaped notch formed at junction of the second leg portion of the substantially L-shaped member and the first end portion of the handle member via one side of the handle member, the first V-shaped notch transversely disposed to an elongated axis of the handle member; and a second V-shaped notch formed at a junction of the second leg portion of the substantially L-shaped member and the first end portion of the handle member via the opposite side of the handle member, the second V-shaped notch transversely disposed to the elongated axis of the handle member and aligned with the first V-shaped notch.

17. The specimen cup holder of claim 16 wherein the second hinge means comprises at least one substantially V-shaped notch formed in the medial portion of the handle member via at least one side thereof, the V-shaped notch being normally disposed relative to the elongated axis of the handle member.

18. The specimen cup holder of claim 17 wherein the ring means, the substantially L-shaped member, and the handle member are of unitary construction fabricated of a polymeric material having sufficient strength to support a specimen cup member positioned within the ring means when the handle member is in the second position.

* * * * *